000000
United States Patent [19]

Henmi et al.

[11] Patent Number: 4,701,327
[45] Date of Patent: Oct. 20, 1987

[54] ETOPOSIDE SOFT CAPSULES

[75] Inventors: Yoshiyasu Henmi, Tokyo; Takashi Terada, Yono; Masaru Suzuki, Tokyo; Hiroshi Ninomiya, Sayama, all of Japan

[73] Assignee: Nippon Kayaku Kabushiki Kaisha, Tokyo, Japan

[21] Appl. No.: 729,993

[22] Filed: May 3, 1985

[30] Foreign Application Priority Data

May 15, 1984 [JP] Japan .................................. 59-95657

[51] Int. Cl.$^4$ .............................................. A61K 9/66
[52] U.S. Cl. .................................................. 424/455
[58] Field of Search ...................... 424/38, 455; 514/33

[56] References Cited

U.S. PATENT DOCUMENTS 3,456,051  7/1969  Mima et al. ........................... 424/37

FOREIGN PATENT DOCUMENTS 2155789A  10/1985  United Kingdom .

OTHER PUBLICATIONS

Chem. Abstracts 97:275w.
Kirk Othmer Encyclopedia p. 507.
Lachman et al., The Theory & Practice of Industrial Pharmacy, 2nd Ed. Veg & Eebiger pp. 408–413.
Falkson et al., "A Clinical Trail of the Oral Form of 4'-Demethyl-Epipodophyllotoxin-$\beta$-D Ethylidene Glucoside," (NSC 141540) VP 16–213, Cancer Apr. 1975, vol. 35, No. 4, pp. 1141–1144.

Primary Examiner—Shep K. Rose
Attorney, Agent, or Firm—Banner, Birch, McKie & Beckett

[57] ABSTRACT

Etoposide soft capsules comprising soft gelatin shells of pH 3.7 to 5.7 and, enclosed therein, an etoposide solution containing an organic acid.

3 Claims, No Drawings

ETOPOSIDE SOFT CAPSULES

BACKGROUND OF THE INVENTION

1. Field of the Invention

This invention relates to etoposide soft capsules comprising soft (elastic) gelatin shells of pH 3.7 to 5.7 and, enclosed therein, an etoposide solution containing an organic acid.

2. Description of the Prior Art

Etoposide, i.e. 4'-demethylepipodophillotoxin-9-(4,6-O-ethylidene-$\beta$-D-glucopyranoside), is a drug effective for treating lung cancer, malignant lymphoma, and testicular tumor.

The etoposide capsule is an already known form of etoposide administration (cancer, April 1975, Vol. 35, No. 4, 1142). In said literature, the internal composition of the capsule is reported to contain 100 mg of etopoisde, 320 mg of Miglyol 812, 70 mg of bee'swax, and 10 mg of soya lecithin, but no mention is made of the capsule shell. In prepairing general capsules, it is a common practice to adjust pH of the shell to an approximate neutrality (pH 7) in view of the stability of the drug. The term "pH of the shell" means pH of an aqueous solution just before forming the shell.

The present inventors carried out a study on encapsulated etoposide preparations. During the study it was found that when a solution of etoposide in polyethylene glycol, for example, is enclosed in common soft gelatin shells of a pH in an approximately neutral range and the resulting capsules are stored, the enclosed etopside manifests instability with the laps of time, resulting in isomerization to picro form.

SUMMARY OF THE INVENTION

The present inventors carried out an extensive study to improve the stability of an encapsulated etopside preparation. As a result, it was found that the stability of etoposide is improved to a large extent by filling soft gelatin shells of a pH in the range of from 3.7 to 5.7 with an etoposide solution containing an organic acid. The present invention has been accomplished on the basis of said finding.

An object of the present invention is to provide stable etoposide capsules.

DETAILED DESCRIPTION OF THE INVENTION

The pH range of the soft gelatin shells used in this invention is from 3.7 to 5.7, usually from 4.0 to 5.5, preferably from 4.4 to 5.5, most preferably from 4.8 to 5.2. The term "pH of the soft gelatin shells", as herein used, means pH of the aqueous gelatin solution just before forming soft capsules.

The organic acid being added to the etoposide solution is not subject to any special restriction but can be any of those acids which are high in physiological safety. Such organic acids include those having 1 to 3 carboxyl groups and 1 to 6 carbon atoms; hydroxycarboxylic acids having a hydroxyl group as substituent can also be used. As examples, mention may be made of citric acid, tartaric acid, malic acid, succinic acid, and fumaric acid. The organic acid may be added in any amount so long as it serves to stabilize the etoposide. The amount generally used is 0.005 to 0.2, preferably 0.01 to 0.1, part by weight for 1 part by weight of etoposide.

The solvent used for dissolving the etoposide and the organic acid is any of those which are liquid at room temperature (25° C.) and capable of dissolving the both components, such as polyhydric alcohols, for example, glycols, glycerol, and polyethylene glycols. Of these alcohols, especially preferred are polyethylene glycoles such as polyethylene glycols 300 and 400. The amount used of the solvent is generally 2 to 50, preferably 5 to 20, most preferably 8 to 15, parts by weight for 1 part by weight of etoposide. These solvents can be used in mixtures of two or more of them. For instance, when a polyethylene glycol is used together with other polyhydric alcohols, a suitable composition of the etoposide solution comprises 8 to 14 parts by weight of the polyethylene glycol, 0.1 to 1.5 parts by weight of other polyhydric alcohols, and 1 part by weight of the etoposide. The etoposide solution may contain, if necessary, auxiliaries such as dissolution aids and stabilizers.

The etoposide capsules according to this invention are prepared as exemplified hereunder.

A gelatin solution of pH 3.7 to 5.7 is prepared by dissolving in water a gelatin produced from an aqueous solution adjusted to pH 3.7 to 5.7 or by dissolving an ordinary grade gelatin (generally pH $\approx 7$) in water and adjusted to pH 3.7 to 5.7 by the addition of pharmacologically acceptable acids such as hydrochloric acid, malic acid, citric acid, tartaric acid, fumaric acid, and lactic acid; these acids are added each alone or in mixtures. To the resulting aqueous gelatin solution, are added, if necessary, plasticizers such as glycerol, propylene glycol, and D-sorbitol; opacifiers or colorants such as ferric oxide, titanium oxide, and dyes; and other additives such as preservatives. The mixture is thoroughly mixed and deaerated to obtain a gelatin solution for capsule shells (hereinafter referred to as solution for capsule shells).

An etoposide solution is prepared by dissolving etoposide and an organic acid in a solvent such as, for example, polyethylene glycol and, if necessary, adding auxiliaries to the resulting solution.

Using the solution for capsule shells and the etoposide solution, the etoposide soft capsules are prepared in a customary manner by allowing their shells formed and filled in succession in one manufacturing procedure; such a procedure is carried out by the plate method or by means of a capsule filler of the rotary die type (see e.g. "Remington's Pharmceutical Sciences" 16 the edition, pages 1580–1582, Mack Publishing Co.)

The excellent stability of the encapsulated etoposide formulation according to this invention is demonstrated in the following example of experiment.

EXAMPLE OF EXPERIMENT (1) Sample: Using 1,200 mg of an etoposide-containing solution (hereinafter referred to as filling solution) and a solution for capsule shells of the following composition, etoposide-containing green capsules were prepared by means of a rotary die process machine of Leiner and Sons Co. The green capsules were dried at 25° C. for 3 days to obtain soft capsules, 23 mm in major diameter and 10 mm in minor diameter, weighing 1,850 mg and containing 100 mg of etoposide:

No. 1 (according to this invention):
Filling solution: A solution of 100 g of etoposide and 5 g of tartaric acid in 1,100 g of polyethylene glycol 400.
Solution for capsule shells: To 10 kg of granular gelatin (pH 6.0), were added 2.5 kg of concentrated glycerin, 0.5 kg of D-sorbitol, 7.5 kg of water, and 180 ml of concentrated hydrochloric acid to form a uniformly wetted mixture. After having been left standing for 12 hours, the swollen mixture was heated to 65° C. and deaerated to form a solution for capsule shells; the pH of the solution was 4.8.

No. 2 (according to this invention):
Filling solution: The same as that of sample No. 1.
Solution for capsule shells: The same as that of sample No. 1, except that the amount of hydrochloric acid was 65 ml; the pH of the solution was 5.4.

No. 3 (according to this invention):
Filling solution: The same as that of sample No. 1.
Solution for capsule shells: The same as that of No. 1, except that 258 g of citric acid was used in place of the concentrated hydrochloric acid; the pH of the solution was 4.9.

No. 4 (according to this invention):
Filling solution: The same as that of sample No. 1, except that 10 g of tartaric acid was used.
Solution for capsule shells: The same as that of sample No. 3.

No. 5 (control):
Filling solution: A solution of 100 g of etopside in 1,100 g of polyethylene glycol 400.
Solution for capsule shells: To 10 kg of gelatin (pH 6.0), were added 2.5 kg of concentrated glycerin, 0.5 kg of D-sorbitol, and 7.5 kg of water. The mixture was treated as in the case of sample No. 1; the pH of the resulting solution was 6.0.

No. 6 (control):
Filling solution: The same as that of sample No. 1.
Solution for capsule shells: The same as that of sample No. 5. (2) Experimental method: Sample Nos. 1 to 4 of the etoposide capsules according to this invention and sample Nos. 5 and 6 for control were stored in press-through packed at room temperature for 12 months. Then each sample was tested for the residual (%) of etoposide and the picro isomer content (%) by high performance liquid chromatography. (3) Results and discussion: The results of experiment were as shown in the following table.

TABLE

Stability of etoposide soft capsules of this invention and control samples in storage for 12 months.

|  | Sample No. | Amount (based on 1 part of etoposide) of organic acid in filling solution | pH of capsule shells | Residual (%) of etoposide | Picro isomer content (%) |
| --- | --- | --- | --- | --- | --- |
| This invention | 1 | 0.05 | 4.8 | 100.3 | 0 |
|  | 2 | 0.05 | 5.4 | 99.2 | 0.7 |
|  | 3 | 0.05 | 4.9 | 99.9 | 0 |
|  | 4 | 0.01 | 4.9 | 99.0 | 0.9 |
| Control | 5 | 0 | 6.0 | 63.3 | 40.1 |
|  | 6 | 0.05 | 6.0 | 90.1 | 9.3 |

It is seen from the results shown in the table that the etoposide soft capsules of this invention showed no decrease in etoposide content and no or slight, if any, formation of the picro isomer. To the contrary, when the filling solution contains no organic acid, as is the case with control sample No. 5, or when the capsule shells of high pH are used, the etoposide content of the capsules showed a markedly decreased value of 63.3%, indicating instability of the encapsulated etoposide.

The method of preparing the etoposide soft capsules according to this invention is illustrated below with reference to Examples, but the invention is not limited thereto.

EXAMPLE 1

A filling solution was prepared by dissolving 3 g of citric acid and 100 g of etoposide in 1,197 g of polyethylene glycol 400.

To 10 kg of a gelation (pH 6.1), were added 2.8 kg of concentrated glycerin, 7.4 kg of water, and 225 ml of concentrated hydrochloric acid to form a thoroughly wetted mixture. After having been left standing for 12 hours, the swollen mixture was heated to 70° C. to form a solution. To the solution, while being stirred, was added a thoroughly mixed suspension of 60 g of titanium oxide as a hiding agent, in 100 g of water to form a solution for capsule shells; the pH of the solution was 4.6.

Using the above solution for capsule shells and each 1,300 mg of the above filling solution, the molding of capsule shells and the filling of capsule shells were simultaneously carried out by means of a rotary die process machine of Leiner and Sons Co. The resulting green capsules were dried at 25° C. for 3 days to obtain filled capsules, each 23 mm in major diameter, 10 mm in minor diameter, and 1,860 mg in total weight including 100 mg of etoposide.

EXAMPLE 2

A filling solution was prepared by adding 10 g of malic acid and 100 g of etoposide to a stirred solution of 30 g of glycerin in 1,120 g of polyethylene glycol 300. Using the solution for capsule shells obtained in Example 1 and each 630 mg of the above filling solution, etoposide soft capsules were prepared in a manner similar to that in example 1. The soft capsules were each 18 mm in major diameter, 8.8 mm in minor diameter, and 990 mg in total weight including 50 mg of etoposide.

EXAMPLE 3

A filling solution was prepared by dissolving with stirring 16 g of tartaric acid and 100 g of etoposide in 1,150 g of polyethylene glycol 400.

To 10 kg of a gelatin (pH 6.0), were added 2.5 kg of glycerin and 7.6 kg of a solution of 300 g of succinic acid in water to form a thoroughly wetted mixture. After having been left standing for 16 hours, the swollen mixture was heated to 65° C. to form a solution. After deaeration under reduced pressure, there was obtained a solution for capsule shells having a pH of 4.3.

Using the above filling solution and the solution for capsule shells, simultaneous molding of capsule shells and filling of each capsule shell with 316.5 mg of the filling solution were carried out by the plate method. The resulting soft capsules were each 17 mm in major diameter, 6.9 mm in minor diameter, and 620 mg in total weight including 25 mg of etoposide.

EXAMPLE 4

A crude gelatin extract obtained by alkali treatment was passed successively through a cation exchange column and an anion exchange column to prepare a gelatin of pH 4.8. To 10 kg of the gelatin, were added 3 kg of glycerin, 100 g of cane sugar, and 7 kg of water to form a thoroughly wetted mixture. After having been left standing for 16 hours, the swollen mixture was heated to 65° C. to form a solution. The resulting solution was deaerated under reduced pressure to obtain a solution for capsule shells having a pH of 4.8.

Using the filling solution obtained in Example 1 and the above solution for capsule shells, simultaneous molding of capsule shells and filling of shells with each 1,300 mg of the filling solution were carried out by means of a rotary die process machine of Leiner and Sons Co. The green soft capsules were dried at 25° C. to a moisture content of 10%. The resulting soft capsules were each 23.2 mm in major diameter, 10.3 mm in minor diameter, and 1,900 mg in total weight including 100 mg of etoposide.

EXAMPLE 5

To a solution of 35 g of glycerin in 1,160 g of polyethylene glycol 400, were added 5 g of citric acid and 100 g of etoposide. The mixture was stirred to obtain a filling solution. Using the filling solution and the solution for capsule shells obtained in Example 1, etoposide soft capsules filled with 1,300 mg of the filling solution were obtained in a manner similar to that in Example 1.

What is claimed is:

1. An etoposide soft capsule comprising a soft gelatin shell of about pH 4.0 to about pH 5.5 having enclosed therein, an etoposide solution containing an organic acid having 1 to 3 carboxyl groups and 1–6 carbon atoms; a solvent of said etoposide solution being a polyhydric alcohol which is liquid at room temperatures.

2. An etoposide soft capsule according to claim 1, wherein the organic acid has 1 to 3 caroxyl groups and 1 to 6 carbon atoms.

3. An etoposide soft capsule comprising a soft gelatin shell of pH 4.8 to 5.2 and, enclosed therein, an etoposide solution comprising (a) 1 part by weight of etoposide, (b) 0.01 to 0.1 part by weight of citric acid, (c) 8 to 14 parts by weight of a polyethylene glycol which is liquid at room temperatures, and (d) 0.1 to 1.5 parts by weight of glycerin.

* * * * *